(12) United States Patent
Evanson (10) Patent No.: US 11,577,900 B2
(45) Date of Patent: Feb. 14, 2023

(54) PACKAGING FOR MICROARRAYS (71) Applicant: KINDEVA DRUG DELIVERY L.P., St. Paul, MN (US)

(72) Inventor: Peter P. Evanson, St. Paul, MN (US)

(73) Assignee: Kindeva Drug Delivery L.P., Woodbury, MN (US)

( * ) Notice: Subject to any disclaimer, the term of this patent is extended or adjusted under 35 U.S.C. 154(b) by 0 days.

(21) Appl. No.: 17/420,918

(22) PCT Filed: Jan. 7, 2020

(86) PCT No.: PCT/IB2020/050087
§ 371 (c)(1),
(2) Date: Jul. 6, 2021

(87) PCT Pub. No.: WO2020/144574
PCT Pub. Date: Jul. 16, 2020

(65) Prior Publication Data
US 2022/0041359 A1 Feb. 10, 2022

Related U.S. Application Data (60) Provisional application No. 62/789,052, filed on Jan. 7, 2019.

(51) Int. Cl.
B65D 77/00 (2006.01)
A61M 37/00 (2006.01)
B65D 75/00 (2006.01)
B65D 75/42 (2006.01)
B65D 81/26 (2006.01)

(52) U.S. Cl.
CPC ....... *B65D 77/003* (2013.01); *A61M 37/0015* (2013.01); *B65D 75/008* (2013.01); *B65D 75/42* (2013.01); *B65D 81/266* (2013.01); *A61M 2209/06* (2013.01)

(58) Field of Classification Search
CPC .... B65D 77/003; B65D 75/008; B65D 75/42; A61M 37/0015; A61M 2209/06; A61B 50/30
USPC .......................................... 206/204
See application file for complete search history.

(56) References Cited

U.S. PATENT DOCUMENTS 5,361,901 A * 11/1994 Schenz ............. H05K 13/0084
206/714
7,659,439 B2 * 2/2010 Grossman ............. A61F 15/002
602/41
7,846,488 B2 12/2010 Johnson et al.
(Continued)

FOREIGN PATENT DOCUMENTS

BE 673340 A 4/1966
CN 104960745 10/2015
(Continued)

OTHER PUBLICATIONS

International Search Report and Written Opinion for PCT/IB2020/050087, issued by the European Patent Office, dated Mar. 31, 2020; 15 pgs.
(Continued)

*Primary Examiner* — Steven A. Reynolds
(74) *Attorney, Agent, or Firm* — Mueting Raasch Group (57) ABSTRACT

A packaging system for microarrays, such as microarrays of microneedles, comprising inner and outer pouches (500, 5000).

14 Claims, 5 Drawing Sheets (56) References Cited

U.S. PATENT DOCUMENTS

| | | | |
|---|---|---|---|
| 8,057,842 B2 | 11/2011 | Choi et al. | |
| 9,144,671 B2 * | 9/2015 | Cantor | A61K 9/0021 |
| 9,789,299 B2 | 10/2017 | Simmers | |
| 9,919,856 B2 | 3/2018 | Yamada | |
| 10,004,567 B2 | 6/2018 | Dacey et al. | |
| 10,201,691 B2 | 2/2019 | Berry et al. | |
| 10,315,021 B2 | 6/2019 | Frederickson et al. | |
| 10,561,831 B2 * | 2/2020 | Kato | A61F 13/00063 |
| 2008/0108958 A1 | 5/2008 | Carter et al. | |
| 2008/0274166 A1 * | 11/2008 | Sacks | A61P 43/00 424/449 |
| 2015/0335870 A1 * | 11/2015 | Quan | A61F 13/0008 604/263 |

FOREIGN PATENT DOCUMENTS

| | | |
|---|---|---|
| CN | 205007427 | 2/2016 |
| CN | 106687171 | 5/2017 |
| CN | 107847723 | 3/2018 |
| EP | 2759313 | 7/2014 |
| EP | 3342447 | 7/2018 |
| JP | 2016140415 | 8/2016 |
| KR | 101288773 | 7/2013 |
| WO | 00/76877 A1 | 12/2000 |
| WO | 03/030984 A1 | 4/2003 |
| WO | 2006/131931 A2 | 12/2006 |

OTHER PUBLICATIONS

International Preliminary Report on Patentability for PCT/IB2020/050087, issued by the European Patent Office, dated Nov. 25, 2020; 14 pgs.

Larrañeta et al., "Microneedle arrays as transdermal and intradermal drug delivery systems: Materials science, manufacture and commercial development," Materials Science and Engineering: R: Reports, Jun. 2016; 104:1-32 pgs.

Korean Office Action issued for KR Application No. 10-2021-7025004 issued by the Korean Patent Office; dated Dec. 1, 2021; 9 pgs. including English translation.

Vinayakumar et al., "A hollow stainless steel microneedle array to deliver insulin to a diabetic rat," Journal of Micromechanics and Microengineering, Jun. 2016;26(6).

Chinese Office Action for CN Application No. 202080008206.2 issued by the China National Patent Office dated Dec. 31, 2022; 7 pgs. including English translation.

* cited by examiner

PACKAGING FOR MICROARRAYS

CROSS-CITED REFERENCE

This application is the § 371 U.S. National Stage of International Application No. PCT/IB2020/050087, filed 7 Jan. 2020, which claims the benefit of U.S. Provisional Application No. 62/789,052, filed 7 Jan. 2019, the disclosures of which are incorporated by reference herein in their entireties.

A variety of microarrays, such as microneedle arrays, have been described in the art, for example U.S. Pat. Nos. 9,144,671, 8,057,842, 7,846,488, 9,789,299, US20170258713, and US20080108958. Complex or expensive custom packaging is described in the prior art as necessary to protect microarrays during transport and storage. For example, Vinayakumar et al. (Journal of Micromechanics and Microengineering, Vol. 26, No. 6, 2016) describe a custom-made poly(methyl methacrylate) package for steel microneedles. Larrañeta et al. (Materials Science and Engineering: R: Reports, Vol. 104, June 2016) report the use of a thin-film membrane to provide closed-package systems.

SUMMARY

A packaging article can comprise a plurality of connected outer pouches, each of the outer pouches made of an outer pouch material, and each of the outer pouch comprising one or more sealed outer pouch edges and one or more outer pouch open edges, wherein at least one of the one or more sealed edges is sealed with a seal that is shared between two adjacent sealed outer pouch edges, each outer pouch comprising an interior and an exterior; and at least one inner pouch, each at least one inner pouch located substantially within an interior of an outer pouch and made of an inner pouch material, the inner pouch comprising at least one sealed inner pouch edge, and at least one open inner pouch edge, the open inner pouch edge being aligned to open towards the open outer pouch edge; wherein the outer pouch material comprises a film having oxygen and water barrier properties. A microarray packaging system can comprise a closed outer pouch having at least one sealed outer pouch edge, the closed outer pouch being completely closed to an external environment; an inner pouch disposed completely within the closed outer pouch, the inner pouch having at least one sealed inner pouch edge and at least one open inner pouch edge; and a microarray device disposed at least partially within the inner pouch and completely within the closed outer pouch.

DETAILED DESCRIPTION

Throughout this disclosure, singular forms such as "a," "an," and "the" are often used for convenience; however, the singular forms are meant to include the plural unless the singular alone is explicitly specified or is clearly indicated by the context. When the singular alone is called for, the term "one and only one" is typically used.

Some terms in this disclosure are defined below. Other terms will be familiar to the person of skill in the art and should be afforded the meaning that a person of ordinary skill in the art would have ascribed to them.

The terms "common," "typical," and "usual," as well as "commonly," "typically," and "usually" and other conjugates of those terms are used herein to refer to features that are often employed in the invention and, unless specifically used with reference to the prior art, are not intended to mean that the features are present in the prior art, much less that those features are common, usual, or typical in the prior art.

Terms of direction, such as "top," "bottom," and the like do not necessarily indicate an absolute direction, for example, with respect to the location of the ground, but rather are used as relative terms to describe the relationship of various components to each other.

Previously known packaging systems for microarray devices typically involve custom-made packaging that is large relative to the size of the microarray device, expensive, and difficult to use in an industrial scale manufacturing setting. There are several technical problems with such systems. First, in practice, such systems necessitate, as part of the manufacturing process, an additional costly decontamination step. Transferring microneedles into precisely made, custom packaging is a slow process so even though microneedles may be decontaminated after being produced a second decontamination after packaging and immediately before sealing may be required. Second, in a manufacturing process, final packaging of microarrays in a large tray is difficult to accomplish at high speed because pick and place machines that pick the microarray device up and place it in the packaging must be designed to place the microarray in multiple locations depending on the particular step in the manufacturing process, which requires more complex machinery and validation of the final packaging process. Third, a variation on the first two problems, is finding a packaging system that permits packaging at a higher rate of speed for faster production. Fourth, prior art packaging systems are typically not convenient for the end user in that it can be difficult to remove the microarray device without extensive handling; this is a technical problem because excessive handling of the microarray device can lead to either damage to the device or to contamination of the device by the user. Fifth, prior-art packaging systems require either custom materials that are not readily available commercially or custom equipment, such as specialized dies, in order to make the packaging systems. Sixth, prior art packaging systems, particularly those that involve the use of large trays, are not conveniently shaped to store and transport, nor are they convenient for the end user, such as a physician or other health care provider, who needs ready access to a predetermined number of microarray devices in a short time span, for example in the setting of providing vaccines via microneedle to a large number of people in a health clinic. Seventh, partially finished microarrays, such as microneedle arrays that are not yet coated with drug, need to be protected from damage during the remaining steps in the manufacturing process, such as coating and sterilization. Formerly known final packaging articles cannot be used for this because it is difficult for pick and place machines to remove and replace microarrays in formerly known packaging articles. Thus, a problem can be providing packaging articles that are compatible with pick and place machines, allowing such machines to take partially finished microarrays out of the article and then return the microarrays to the packaging article after manufacturing steps are performed on the microarrays.

Briefly, a solution to one or more of the above problems, which is described in further detail herein, lies in a packaging article with a plurality of connected outer pouches, each of the outer pouches comprising one or more sealed outer pouch edges and one or more outer pouch open edges, wherein at least one of the one or more sealed outer pouch open edges is sealed with a seal that is shared between two adjacent sealed outer pouch edges. Each outer pouch comprises an interior and an exterior. At least one inner pouch is also present, each at least one inner pouch being located at least substantially within the interior of one of the plurality of connected outer pouches and comprising at least one sealed inner pouch edge and at least one open inner pouch edge.

The open inner pouch edge is aligned towards the open outer pouch edge, which allows for a microarray device to be placed within both the inner and outer pouches. Bearing this purpose in mind, an inner pouch can be deemed to be substantially within the interior of an outer pouch if a microarray device comprising microneedles is placed within the inner pouch is disposed such that microneedles of the microarray device are within both the inner and outer pouches. Other portions of the microarray device, such as the handle, may protrude from the inner pouch, the outer pouch, or both. In many cases, the outer pouch not be fully sealed during the manufacturing process of the microarray device, but will then be sealed, with the microarray device fully enclosed by the outer pouch, after the manufacture of the microarray device is complete. Some steps, such as sterilization, for example e-beam sterilization, can be completed after the microarray device is fully sealed within the packaging article.

The outer pouch comprises an outer pouch material that has oxygen and water barrier properties, that is, the outer pouch material acts as a barrier to oxygen and water.

A packaging article can include a plurality of outer pouches. The plurality of outer pouches can share a single bottom, which can be made by folding a sheet of the outer pouch material, or by bonding together multiple sheets of outer pouch material. Bonding can be accomplished by heat fusing, gluing, etc. A gusset can be present in the bottom, for example to allow the packaging article to stand upright. Gussets can be formed by folding and joining two or more appropriately sized pieces of outer pouch material.

At least one sealed outer pouch edge is shared by at least two adjacent outer pouches. The sealed pouch edge can be formed by heat sealing, gluing, etc. It is possible to have only two outer pouches in a packaging article, but any practical number of outer pouches can be provided. For example, 5, 10, 50, 100, 250, 500, 750, 1,000, 1,250, 1,500, 1,750, 2,000, or even more outer pouches can be present in a single packaging article. Such large numbers of pouches can be convenient for use in manufacturing. If the number of pouches in the packaging system provides a packaging system that is too long or contains too many microarray devices to conveniently transport or store, or for the convenience of the end user, then the length of the system or the number of pouches can be reduced by cutting on one of the sealed edges, so long as the interiors of the outer pouches adjacent to the sealed edges are not infringed upon.

The outer pouch material can protect the microarray device from has oxygen and water barrier properties, such that it acts as a barrier to oxygen and water. It is not necessary that the outer pouch exclude all oxygen and water, only that the transmission of oxygen and water through the outer pouch be sufficiently retarded such that the microarray device, including any drug that may be present on the microneedles, is not unacceptably degraded during transport and storage. Thus, the requirements of the outer pouch material will depend on the specifications of the particular microarray device being used.

One or more sealed outer pouch edge can contain at least one indexing hole. The indexing holes can serve several purposes. They can also act as a guide for equipment, such as a pick and place machine, to locate an interior of an outer pouch for example to place an interior pouch or a microarray device therein. They can indicate to a machine or a user where to separate the individual pouches containing microarray devices. They can act as a tear start for a user to open the packaging.

Typical outer pouch materials comprise at least one layer. The at least one layer will often comprises a material such as polyesters, for example poly(ethylene terephthalate), polyethylene, such as low density polyethylene, ultra-low density polyethylene, linear low density polyethylene (LL-DPE), high density polyethylene, or the like, metal foil, often aluminum foil, polypropylene, polyamides, such as nylon 6,6, poly(vinylene chloride), polystyrene, and the like. In many cases, the outer pouch material is a multi-layer material. The at least one layer may comprise polyester, polyethylene, metal foil, propylene polyamide, or polystyrene, or a combination thereof. In many cases, the outer pouch material is a multi-layer material. Whether single or multi-layer, the outer pouch material can comprise at least one poly(ethylene terephthalate) layer (PET layer). Whether single or multi-layer, the outer pouch material can comprise at least one polyethylene layer. Whether single or multi-layer, the outer pouch material can comprise at least one linear low density polyethylene layer. Whether single or multi-layer, the outer pouch material can comprise at least one metal foil layer, typically aluminum foil. One outer pouch material that can be used comprises a laminate film having an exterior layer of poly(ethylene terephthalate) on a layer of polyethylene, an interior layer of linear low density polyethylene on a layer of polyethylene, and an aluminum foil layer between the two layers of polyethylene. This material is sold under the trade designation PFP400W and is available from Texas Technologies (Cedar Park, Tex., USA).

The inner pouch has at least one sealed inner pouch edge, which can be made either by folding a single sheet of inner pouch material or by joining two or more sheets of inner pouch material. Joining can be accomplished in the same manner as described above with respect to the outer pouches. The inner pouch is located within an outer pouch and oriented such that the open edges of the inner pouch are aligned with the open outer pouch edges. This allows a microarray device to be placed inside the inner pouch interior through the openings in the outer pouch and the inner pouch. Typically, the interior of each of the outer pouches will contain an inner pouch, though this is not required in all cases. For example, it can be convenient to include a packaging article that has inner pouches and microarray devices within some of the outer pouches and one or more microneedle applicators within other outer pouches, in which case the outer pouches that contain microneedle applicators may not require an inner pouch. In most cases, no more than one inner pouch is contained within any outer pouch; however, this is not required in all cases because two inner pouches can be used if required to provide extra protection against physical damage to the microarray device.

The inner pouch is located within the outer pouch. In most cases, the inner pouch sits inside the outer pouch without being fixed in place. However, the inner pouch can also be affixed to the outer pouch material on the inside of the outer pouch. This can be accomplished, for example, by use of an adhesive or by heat sealing, among other ways.

The inner pouch material is typically a rigid material that provides some protection of the microneedles from breaking during packaging, handling, transportation, and storage. While a variety of rigid plastic materials may be used for the inner pouch materials, it has been surprisingly found that paper stock or card stock, such as the stock used to make index cards or manila filing folders, offers sufficient rigidity and provides adequate protection against physical damage for this purpose. It is also possible to imbed a desiccant, such as silica gel or molecular sieves, within the inner pouch material; this can be useful when a drug that is coated on the microneedle has a high degree of moisture sensitivity, but it is not required in all cases. Imbedding desiccant in an inner pouch material may be accomplished by any suitable method. Suitable inner pouch materials with imbedded desiccant, for example 0026 ACTIV-FILM (CSP Technologies, Auburn, Ala., US), are commercially available.

One or more features, for example a notch, a hole, a slit, a tab, or more than one of the foregoing, can be present anywhere in the inner pouch, including an upper portion, lower portion, or the sealed edge. These features can be designed to interact with one or more portions of the microarray device, for example, to help keep the device oriented within the inner pouch.

The dimensions of the packaging article can be adjusted to accommodate the needs of the microarray device to be packaged. A typical microarray device includes a microarray holder, which is typically plastic but can be any suitable material including metal or others, that carries a microneedle patch. The microneedle holder often includes a handle for convenient handling and may also include other features such as rails that can interact with an applicator in use. The handle or other features can also interact with the features in the inner pouch, such as a notch, slit, hole, or tab, if present. For example, a handle on the microarray device can interact with a notch on the inner pouch to keep the handle oriented towards the open inner and outer pouch edges for ease of use.

The microneedle patch is typically in the form of a backing with microneedles protruding therefrom. The term "microneedles" refers to needles or similar projections having a size on the microscale; other disclosures have used the term "microprotrusions" in the same sense, in which case the term microneedles is intended to include such microprotrusions. Microneedles can be hollow or solid, and can be wholly or partially dissolvable within the body. When hollow, the microneedles will often contain one or more active agents, often along with optional excipients, within the microneedles, or they may not contain any active agents and may be used to infuse active agents from a reservoir into the body. When solid, the microneedles will often contain a coating of one or more active agents, often along with optional excipients. When dissolvable, the microneedles will often be made out of a dissolvable matrix having one or more active agents, often along with optional excipients, in the matrix.

In use, an inner pouch can be placed inside of each outer pouch of a plurality of outer pouches. Microneedle arrays can then be placed within the inner and outer pouches. The outer pouches can then be sealed, for example by heat sealing, laminating, or the like. After sealing, a user or machine can then cut the sealed edges between the connected sealed outer pouches, such as through the indexing holes, in order to form individual pouches, typically each containing a microarray device. The individual pouches include an outer pouch that is closed on all sides, that is, all of the sides of the pouch have sealed outer pouch edges and none of the sides have open outer pouch edges (typically there are four edges, but other shapes are possible), and an inner pouch within the outer pouch, the inner pouch having at least one open inner pouch edge and at least one sealed inner pouch edge. A microarray device resides within the inner pouch. The former indexing holes, now cut through, take the form of indentations near a sealed edge outer pouch edge. These indentations can make it easier for a user to tear or cut open a sealed outer pouch edge of the outer pouch. A desiccant may also be placed within the outer pouch along with the microarray device. This configuration is different from other dual-pouch systems in that the inner pouch has at least one open inner pouch edge and thus is not completely sealed, but the outer pouch is sealed to the external environment. The advantages discussed herein also apply to the system once it is sealed and cut into individual packages.

Figure 1:
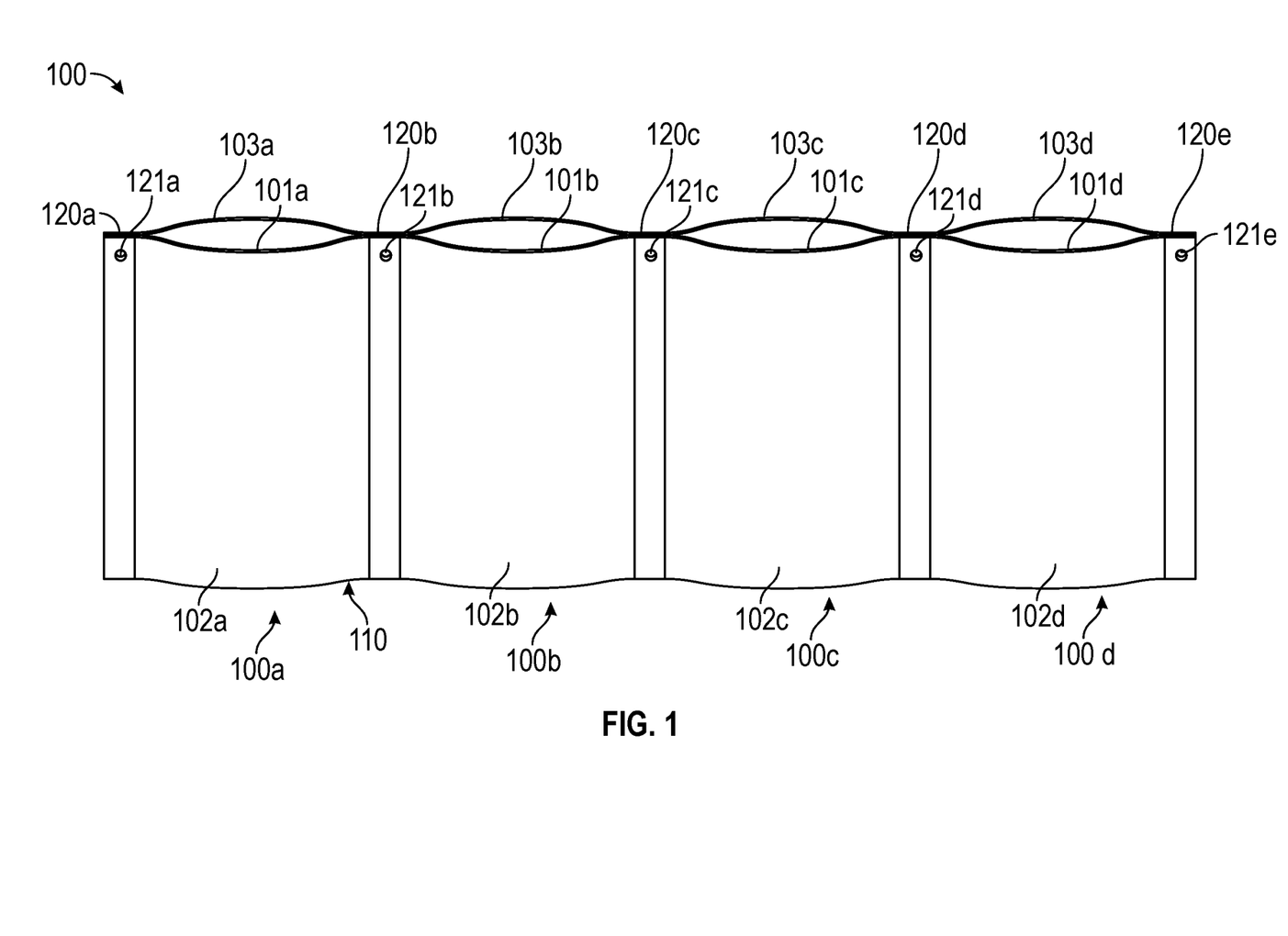
FIG. 1 shows an exemplary packaging article.

Turning to the Figures, which show illustrative features of packaging articles and are not necessarily to scale, FIG. 1 shows an exemplary packaging article 100, which in this figure includes four outer pouches 100a, 100b, 100c, and 100d, each of which comprises interior 101a, 101b, 101c, and 101d, respectively, and exterior 102a, 102b, 102c, and 102d, respectively. Sealed edge 110 defines a bottom of outer pouches 100a, 100b, 100c, and 100d. Sealed edges 120a, 120b, 120c, 120d, and 120e define the sides of the outer pouches.

Open edges 103a, 103b, 103c, and 103d define openings in the outer pouches 100a, 100b, 100c, and 100d, respectively, for placing items within an interior 101a, 101b, 101c, or 101d of one or more of outer pouches 100a, 100b, 100c, and 100d.

Each of sealed outer pouch edges 120b, 120c, and 120d is shared between two adjacent outer pouches. Each sealed outer pouch edge 120a, 120b, 120c, 120d, and 120e comprises indexing holes 121a, 121b, 121c, 121d, and 121e, none of which communicate with interiors 101a, 101b, 101c, or 101d. It should be noted that while the indexing holes are not required in all cases, they can provide several advantages including allowing a machine, such as a pick-and-place machine, to identify the location of the openings in the outer pouches 100a, 100b, 100c, and 100d, to allow packaging machines to align multiple packaging articles 100, for example in a box, and so forth. Other advantages of indexing holes are most apparent when the packaging system 100 is in use, and are discussed in more detail below.

Figure 2:
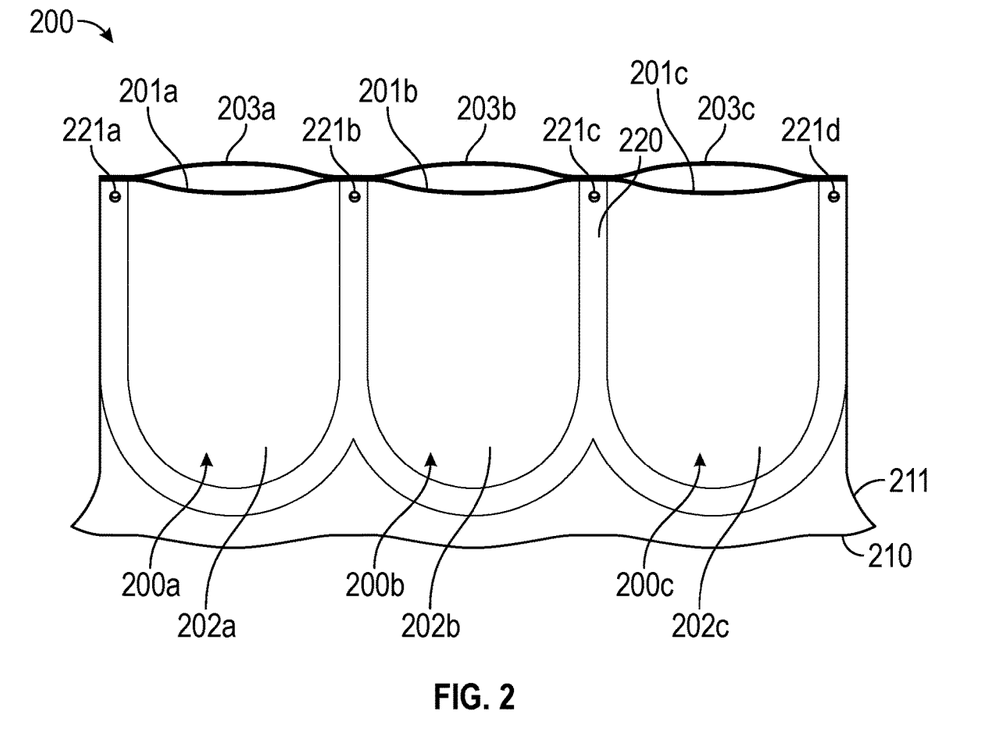
FIG. 2 shows another configuration of an exemplary packaging article.

A different configuration is shown in FIG. 2 wherein packaging article 200 includes three outer pouches 200a, 200b, and 200c, the outer pouches 200a, 200b, and 200c respectively including interiors 201a, 201b, and 201c as well as exteriors 202a, 202b, and 202c. Outer pouch open edges 203a, 203b, and 203c define openings in outer pouches 200a, 200b, and 200c, respectively.

A single sealed outer pouch edge 220 is configured so that it defines the sides as well as the bottom of each of outer pouches 200a, 200b, and 200c. Sealed outer pouch edge 220 includes indexing holes 221a, 221b, 221c, and 221d.

Bottom 210 of packaging system 200 does not define any of interiors 201a, 201b, or 201c, but is instead equipped with gusset 211 which permits packaging system 200 to readily stand upright unaided. While not shown in the figures, it is possible to equip any embodiment with a gusset in a similar manner as packaging system 200.

Any bottom of the plurality of outer pouches can be conveniently made by appropriately folding a sheet of outer pouch material, or alternatively by fusing, such as heat fusing, two sheets of outer pouch material. If a gusset is present, it can be achieved by any suitable means, such as by heat fusing multiple pieces of outer pouch material to form the gusset. The sealed outer pouch edges or edges can be formed by any suitable means, such as by heat fusing the appropriate portions of the outer pouch material to form the shape of the plurality of outer pouches. The open outer pouch edges in most cases represent the edges of one or more sheets of outer pouch material that have not been joined together or fused.

Figure 3A:
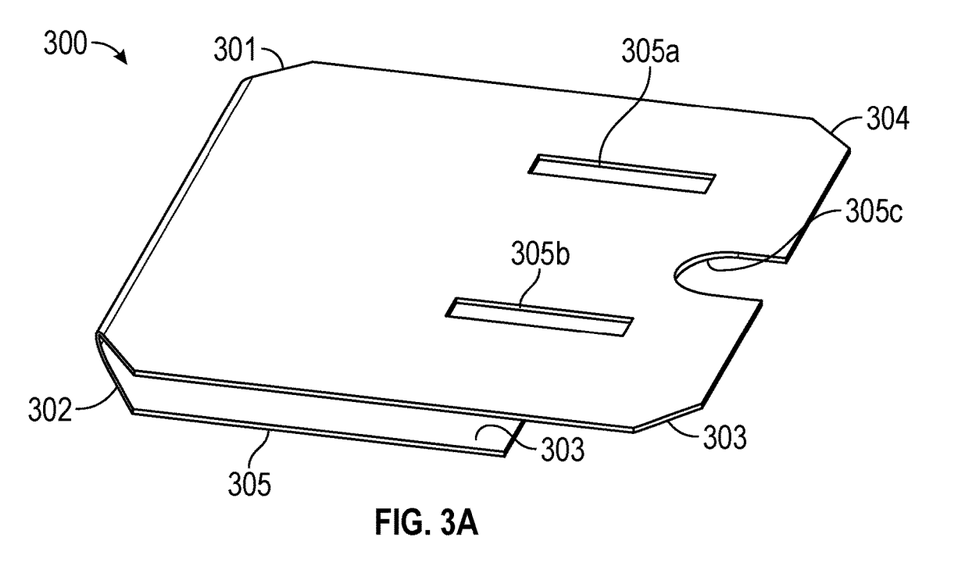
FIG. 3A is a three-quarter view of an inner pouch of a packaging article.

FIG. 3A is a three-quarter view of inner pouch 300, showing opposing first open inner pouch edge 304, which along with sealed inner pouch edge 302, top portion 301 and bottom portion 305 define inner pouch interior 303. Also shown are interior pouch features 305a, 305b, and 305c, which in this Figure are located on top portion 301 and are in the form of holes 305a and 305b and notch 305c. Such interior pouch features are shown in this Figure but are not necessarily present in all cases. Inner pouch interior 303 is available for placing, for example, a microarray device.

Figure 3B:
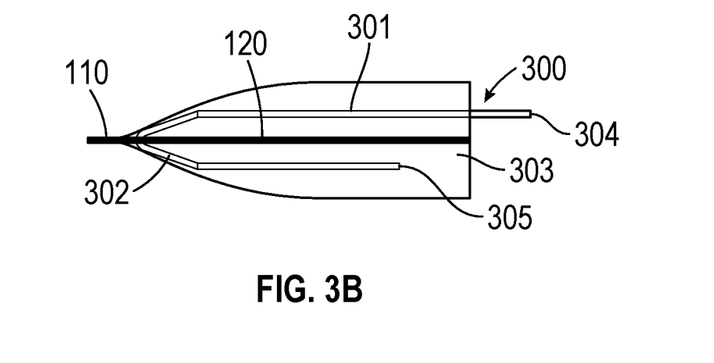
FIG. 3B is a side profile view of inner pouch.

FIG. 3A shows top portion 301 being protruding beyond the end of bottom portion 303. Two additional configurations (not shown) are possible. One additional configuration features top portion 301 and bottom portion 303 being of equal length. The additional configuration is particularly preferred in some cases, for example, because in this configuration it may not be necessary to control the orientation of the top and bottom portions 301 and 303 within the outer pouch. This is especially true if interior pouch features, such as holes 305a and 305b and notch 305c are not present. A second additional configuration features bottom portion 303 being longer than top portion 301. The second additional configuration is particularly advantageous in some cases, because in this configuration the longer lower portion 303 may be used to guide a microarray device into the inner pouch without the microarray device snagging on notch 305c of upper portion 301 FIG. 3B is a side profile view of inner pouch 300 within outer pouch edge 110, which can be an edge of an outer pouch, for example outer pouch 101a (as shown in FIG. 1A) or outer pouch 200a (as shown in FIG. 2). Inner pouch 300 features top portion 301, sealed inner pouch edge 302, and open inner pouch edge 304, as well as bottom portion 305. Inner pouch interior 303 is available for placing a microarray device. In this Figure, sealed inner pouch edge 302 rests on sealed outer pouch edge 110, but that is not necessary.

Figure 4:
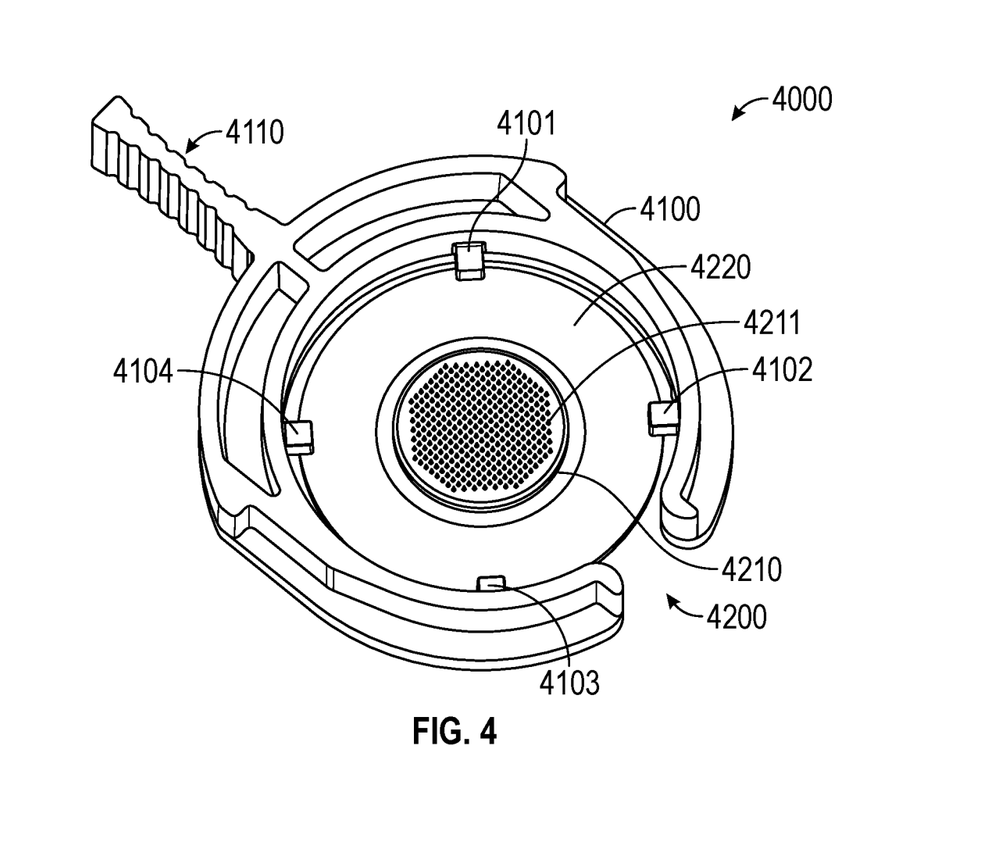
FIG. 4 is a three-quarter bottom view of microarray device.

FIG. 4 is a three-quarter bottom view of microarray device 4000, which is an exemplary microarray device that can be packaged in the packaging article described herein. Microarray device 4000 includes microarray holder 4100 as well as microneedle patch 4200. Microneedle patch 4200 includes a central portion 4210 featuring a plurality of microneedles 4211 disposed on flexible backing 4220. While the central portion 4210 is shown as being roughly circular, other shapes are possible. Further, whereas the plurality of microneedles 4211 are shown as being arranged in a particular manner, other arrangements are possible. Any suitable number of microneedles can be used, and the microneedles may be solid, hollow, or a mixture of solid and hollow. When the microneedles are solid microneedles, such as those described in U.S. Pat. No. 9,789,299, then the microneedle patch 4200 typically has 90 to 1,200 microneedles, such as greater than 200 microneedles, greater than 300 microneedles, greater than 400 microneedles, less than 500 microneedles, or less than 400 microneedles on the patch, although any desired number of microneedles can be used. When the microneedles are hollow, such as those described in U.S. Pat. No. 10,201,691, then the microneedle patch 4200 typically has 3 to 30 microneedles, most often 12 microneedles, although any desired number of microneedles can be used.

Tabs 4101, 4102, 4103, and 4104 serve to retain a microneedle patch and, in this figure, are retaining microneedle patch 4200. Microneedle patch 4200 may also be affixed to tabs 4101, 4102, 4103, and 4104 by way of an adhesive, though this is not required in all cases. Handle 4110 is a convenient feature for manipulating microarray holder 4100.

Figure 5:
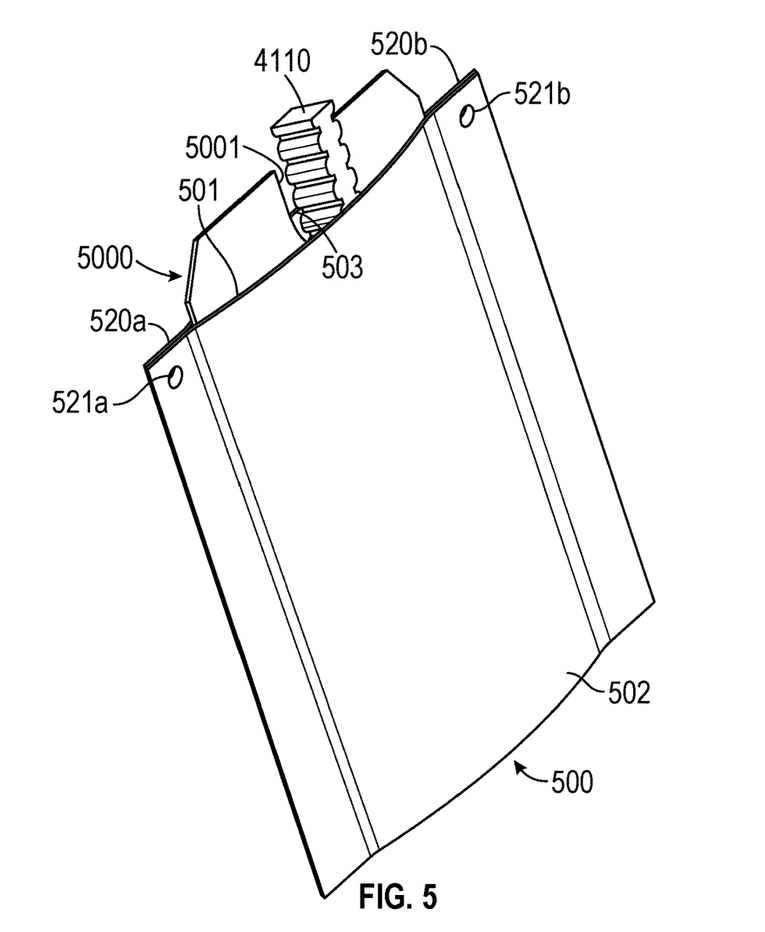
FIG. 5 is a three-quarter view of a portion of a packaging article.

FIG. 5 is a three-quarter view of a portion of a packaging article featuring outer pouch 500, which can be one of a plurality of outer pouches of any of the packaging articles disclosed herein. Outer pouch 500 includes sealed outer edge 502, sealed edges 520a and 520b respectively having indexing holes 521a and 521b, and open outer edges 501 and 503. Inner pouch 5000, which can be similar to inner pouch 300, and has notch 5001, is disposed within outer pouch 500. Microarray device 4000 is disposed within interior pouch such that handle 4110 is visible and is aligned with notch 5001.

Figure 6:
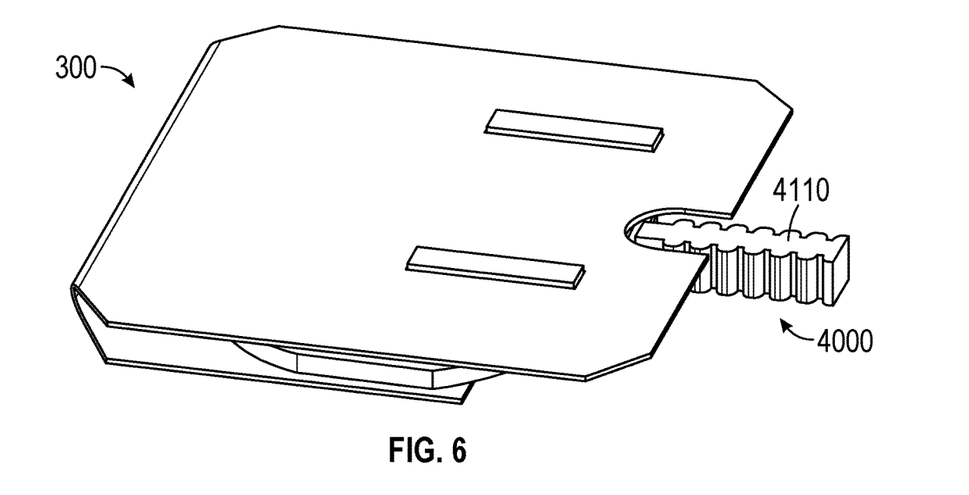
FIG. 6 is a three-quarter bottom view of microneedle array device within an interior pouch of a packaging article.
Figure 7:
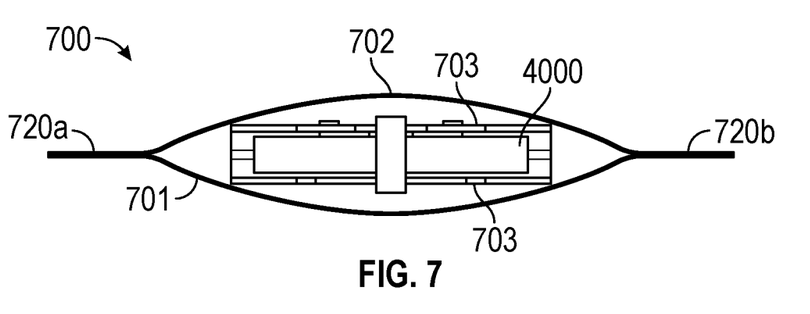
FIG. 7 is a top-down view of a portion of a packaging article.

FIG. 6 is a three-quarter bottom view of microneedle array device 4000 within an interior pouch 300. FIG. 7 is a top-down view of a portion of a packaging article featuring outer pouch 700, which can be one of a plurality of outer pouches of any of the packaging articles disclosed herein, having sealed edges 720a and 720b, as well as outer pouch open edges 701 and 702. Inner pouch 703 resides inside outer pouch 700, and microarray device 4000 in turn resides within inner pouch 703.

Packaging articles as described herein are easy to manufacture. The outer pouch can be produced, for example, from a roll of outer pouch material using conventional techniques such as folding, sealing, and laminating. The inner pouches can be produced in the same way, or, when they are made of paper stock or card stock, by well-known techniques for manufacturing paper or card stock products, such as cutting, stamping, folding, and the like.

The packaging article described here uses less packaging material than the trays, such as plastic trays, which designed specifically to enclose the microarray device and render it immobile. Thus, they can address the problem of manufacturing a packaging article without the use of excess plastic, and without the need to design an article that is specific to the microarray device being packaged.

Further, it is easier for the user to use the packaging article disclosed herein because a handle of the microarray device can extend out of the inner pouch for easy removal of the microarray device from the packaging, whereas custom trays that fit tightly around the microarray device may render it difficult to remove the device from the tray.

Another advantage of the packaging articles described herein is in the manufacturing process of the microarray device, particularly coated microarray devices. The packaging articles herein are particularly well suited for use with pick and place machines. Thus, in a microneedle manufacturing process, it is possible to store uncoated microneedles in their individual places (i.e., within inner pouches of the packaging article), remove them in order to subject them to a manufacturing step, such as coating or drying, and then return them to their place within the inner pouch. This is much more efficient than current processes, which can require separate packaging for the coated and coated microneedles and do not permit returning partially finished microneedles to the packaging between manufacturing steps.

EXAMPLES

Example 1. Strip of Outer Pouches

A strip of six outer pouches in the format as described in FIG. 1A was prepared by folding in the horizontal direction a sheet of white laminated PET/aluminum foil/LLDPE poly barrier film (obtained as PFP400W film from Texas Technologies, Cedar Park, Tex.). The PFP400W film was reported by the manufacturer to have a film thickness of 4.0 mils (0.1 mm), MVTR (moisture vapor transmission rate) of 0.0006 grams/100 square inches/24 hours, and an OTR (oxygen transmission rate) of 0.0006 $cm^3$/100 square inches/24 hours). The film was folded so that the white PET surface formed the exterior of the strip. Heat sealing in the vertical direction provided the side walls of the six outer pouches. Each pouch had a height of about 8.25 cm and a width of about 4.45 cm. The width of the heat sealed section between each pouch was about 19 mm. Each pouch had one open end. Indexing holes (6.3 mm diameter) were centered and punched in the heat sealed sections about 9 mm from the edge of the open end.

Example 2. Individual Outer Pouches

Individual outer pouches were cut from the strip of pouches in Example 1 by making vertical cuts extending through the heat sealed sections. The cuts were aligned to cross through the centers of the indexing holes. These cuts resulted in the creation of a notches on the sides of the separated pouches.

Example 3. Microarray Device

The microarray holder (4100 of FIG. 4) of the microarray device (4000 of FIG. 4) was molded from polypropylene in the form presented in FIG. 4. The opening along the perimeter of the holder was about 10 mm and the overall thickness of the section of the holder for containing a patch was about 5.4 mm. The four tab sections (4101-4104 of FIG. 4) were evenly spaced with each tab having dimensions of 2 mm by 2 mm. The distance between opposing tabs (i.e. distance between tabs 4101 and 4103 and the distance between tabs 4102 and 4104 of FIG. 4) was about 24.4 mm. The handle section had dimensions of about 15.7 mm (length), 8 mm (width), and 2.3 mm (depth). The handle contained 7 ribbed sections.

The central portion (4210 of FIG. 4) of the microneedle patch (4200 of FIG. 4) was injection molded from Class VI, medical grade liquid crystalline polymer (LCP) (VECTRA MT1300, Ticona Plastics, Auburn Hills, Mich.) as a rigid disk about 12 mm in diameter. One side of the disk featured 316 four-sided pyramidal-shaped microneedles arranged in an octagonal pattern that was centered on the disk. The microneedles had heights of about 500 microns, an aspect ratio of about 3:1, and a tip-to-tip distance between neighboring microneedles of about 550 microns.

The microneedle patch was constructed by attaching the side of the disk opposite from the microneedles to the adhesive surface of a flexible backing (26.5 mm in diameter). The disk was centered on the backing leaving a ring of adhesive covered backing surrounding the perimeter of the disk. The opposite side of the backing did not have an adhesive surface.

Microarray devices were prepared by inserting a finished microneedle patch into the internal opening of a microarray holder so that the adhesive surface of the microneedle patch was in contact with the four tabs of the microarray holder.

Example 4. Inner Pouch

A simple fold was made in a single sheet of card stock having a thickness of 0.23 mm (9 mils) to create a rectangular shaped inner pouch having one sealed edge. The width was about 3.2 cm (measured along the folded edge) and height was about 4.2 cm.

Example 5. Inner Pouch

A simple fold was made in a single sheet of PET having a thickness of 0.76 mm (30 mils) to create a rectangular shaped inner pouch having one sealed edge. The width was about 3.2 cm (measured along the folded edge) and the height was about 4.2 cm.

Example 6. Inner Pouch

A simple fold was made in a single sheet of M-0026 ACTIV-FILM obtained from CSP Technologies, Auburn, Ala. and having a thickness of 0.76 mm (30 mils), to create a rectangular shaped inner pouch having one sealed edge. The width was about 3.2 cm (measured along the folded edge) and the height was about 4.2 cm. The M-0026 ACTIV-FILM contained imbedded 4 angstrom molecular sieves as desiccant material.

Example 7A-7C. Inner Pouch

A single sheet of card stock having a thickness of 0.23 mm (9 mils) was folded to create an inner pouch having a sealed edge with a box bottom configuration and open edges on the remaining sides. The dimensions of the top and bottom portions of the pouch were about 4.2 cm (height) and about 3.2 cm (width). The dimensions of the box bottom section of the pouch were about 3.2 cm by about 5.5 mm. This inner pouch is Example 7A.

Inner pouches with the same dimensions were also prepared according to this procedure using PET film (thickness 0.76 mm (30 mils); Example 7B) and M-0026 film (thickness 0.76 mm (30 mils); Example 7C) in place of the card stock.

Example 8. Inner Pouch

A simple fold was made to a single sheet of card stock having a thickness of 0.23 mm) (9 mils) to create a rectangular shaped inner pouch having one sealed edge. The dimensions of the top and bottom portions of the pouch were about 3.8 cm width (along the folded edge) and height of about 4.8 cm. A half-circle shaped notch (4 mm diameter)

was cut into the top portion of the pouch and centered on the edge opposite from the sealed (folded) edge (305c of FIG. 3A). Two rectangular shaped holes (each 8 mm by 2 mm) were also cut into the top portion of the pouch (305a and 305b of FIG. 3A). Each hole was oriented so that the elongated sides of the holes were parallel to the side edges of the pouch. Each hole was positioned 3 mm below the bottom of the notch and about 6 mm from a side edge of the pouch. The holes were positioned to align with two rectangular alignment features (each 7.4 mm by 1.8 mm) protruding from the surface of the microarray holder. The corners of the pouch were trimmed to provide slightly rounded edges.

Example 9. Inner Pouch

The same procedure to prepare an inner pouch as reported in Example 8 was followed with the exception that an asymmetric fold was created so that the top portion of the pouch had smaller dimensions (width of about 3.8 cm and height about 4.8 cm) than the bottom portion of the pouch (width of about 3.8 cm and height about 5.6 cm).

Example 10. Inner Pouch

The same procedure to prepare an inner pouch as reported in Example 8 was followed with the exception that an asymmetric fold was created so that the top portion of the pouch had larger dimensions (width of about 3.8 cm and height about 5.6 cm) than the bottom portion of the pouch (width of about 3.8 cm and height about 4.8 cm).

Example 11. Inner Pouch

A sheet of card stock having a thickness of 0.23 mm (9 mils) was asymmetrically folded to create an inner pouch having a sealed edge with a box bottom configuration and open edges on the remaining sides. The dimensions of the top portion were width of 4.0 cm (measured along sealed edge) and height of 4.0 cm, while the dimensions of the bottom portion were width of 4.0 cm (measured along sealed edge) and height of 6.0 cm. The dimensions of the box bottom section of the pouch were 4.0 cm by 7 mm.

A small, half-circle shaped notch was cut into the top portion of the pouch and centered on the edge opposite from the sealed (folded) edge (305c of FIG. 3A). Two rectangular shaped holes (each 8 mm by 2 mm) were also cut into the top portion of the pouch (305a and 305b of FIG. 3A). Each hole was oriented so that the elongated sides of the holes were parallel to the side edges of the pouch. Each hole was positioned about 5 mm from the edge containing the notch and about 7 mm from a side edge of the pouch. The holes were positioned to align with two rectangular alignment features (each 7.4 mm by 1.8 mm) protruding from the surface of the microarray holder. In some configurations, the corners of the pouch were trimmed to provide slightly rounded edges.

Example 12. Inner Pouch

A single sheet of M-0026 ACTIV-FILM having a thickness of 0.76 mm (30 mils) thick) was asymmetrically folded to create a rectangular shaped pouch with one sealed edge. The dimensions of the top portion were width of 4.0 cm (measured along sealed edge) and height of 4.5 cm, while the dimensions of the bottom portion were width of 4.0 cm (measured along sealed edge) and height of 5.0 cm. The top portion was trimmed to create a trapezoid shape tab centered on the edge opposite from the sealed (folded) edge. The tab was about 2.2 cm wide at the base and about 1.6 cm wide at the top edge. The height of the created tab was about 1.3 cm. A corresponding dove-tail oriented, trapezoid shaped notch (with matching dimensions to the tab) was cut in the bottom portion and centered on the edge opposite from the sealed (folded) edge.

Example 13. Packaging Article

A single inner pouch from Example 4 placed in each outer pouch of the strip of pouches prepared in Example 1. Each inner pouch was oriented so that the folded edge of the inner pouch faced the folded (bottom) edge of the outer pouch.

Example 14. Packaging Article

Packaging articles were prepared as described in Example 13 using inner pouches selected from Examples 5-12 in place of the inner pouch of Example 4.

Example 15. Packaging Article Including Microarray Device s

A single microarray device of Example 3 was inserted in each of six inner pouches of Example 4. A single inner pouch containing a microarray device was placed in each outer pouch of the strip of pouches prepared in Example 1. Each inner pouch was oriented so that the folded edge of the inner pouch faced the folded (bottom) edge of the outer pouch. Each microarray device was oriented so that the handle region of the device extended beyond the inner pouch and faced the open end of the outer pouch.

Example 16. Packaging Article Including Microarray Devices

Packaging articles were prepared as described in Example 15 using inner pouches selected from Examples 5-12 in place of the inner pouch of Example 4. For examples where the inner pouch contained a notch, the handle region of the microarray device was aligned with the notch and faced the open end of the outer pouch.

Example 17. Puncture Test of Microneedle Packaging System

A single microarray device of Example 3 was inserted into an inner pouch of Example 8. The single inner pouch containing a microarray device was placed in an individual outer pouch prepared according to Example 2. The inner pouch was oriented so that the folded edge of the inner pouch faced the folded (bottom) edge of the outer pouch. The microarray device was oriented so that the handle region of the device was aligned with the notch of the inner pouch and faced the open end of the outer pouch. The two alignment features on the device were also positioned to be in alignment with the two holes (305a and 305b) of the inner pouch. The open end of the outer pouch was then heat sealed resulting in the inner pouch with inserted microarray device being completely enclosed by the sealed outer pouch.

The pouch was placed on a carpeted floor and oriented so that the microneedles of the device faced the floor. A weight of 104.3 kg (230 pounds) was applied for five seconds to a 7.6 cm by 7.6 cm section directly over the position of the microarray device in the pouch. Subsequent inspection of the outer pouch by visual examination showed slight indents, but no punctures of the outer pouch.

The invention claimed is:

1. A packaging article comprising:
 a plurality of connected outer pouches, each of the outer pouches made of an outer pouch material, and each of the outer pouches comprising one or more sealed outer pouch edges and one or more outer pouch open edges, wherein at least one of the one or more sealed edges is sealed with a seal that is shared between two adjacent sealed outer pouch edges, each outer pouch comprising an interior and an exterior; and
 at least one inner pouch, each at least one inner pouch located substantially within an interior of at least one of the outer pouches and made of an inner pouch material, the inner pouch comprising:
  at least one sealed inner pouch edge; and
  at least one open inner pouch edge, wherein the open inner pouch edge is aligned with the open outer pouch edge;
 wherein the outer pouch material comprises a film having oxygen and water barrier properties;
 wherein at least one of the inner pouches contains a microarray device, the microarray device comprising:
  a microneedle patch comprising a backing having a first major surface, a second major surface, and one or more microneedles protruding from the first major surface of the backing; and
  a microneedle holder that holds the microneedle array backing.

2. The packaging article of claim 1, wherein the inner pouch material comprises paper stock or card stock.

3. The packaging article of claim 1, wherein no more than one inner pouch is contained within the interior any one of the connected outer pouches.

4. The packaging article of claim 1, wherein a plurality of the connected outer pouches each comprise one of the at least one inner pouches within their interiors.

5. The packaging article of claim 1, wherein at least one of the one or more sealed edges of the connected outer pouches comprises one or more indexing holes that do not communicate with the interior of any of the connected outer pouches.

6. The packaging article of claim 1, wherein the at least one inner pouch comprises a feature selected from a notch, a slit, a hole, or a tab.

7. The packaging article of claim 1, wherein the outer pouch material comprises at least one poly(ethylene)terephthalate layer.

8. The packaging article of claim 1, wherein the outer pouch material comprises at least one metal foil layer.

9. The packaging article of claim 1, wherein the outer pouch material comprises at least one polyethylene layer.

10. The packaging article of claim 1, wherein the outer pouch material comprises at least one linear low density polyethylene layer.

11. The packaging article of claim 1, wherein the microneedle array holder further comprises a handle for manipulating the microneedle array device.

12. The packaging article of claim 1, wherein the microneedle array holder further comprises at least one feature selected from a ridge, a tab, a rail, and an embossment.

13. The packaging article of claim 6, wherein the microneedle array holder further comprises a handle for manipulating the microneedle array device and at least one feature selected from a ridge, a tab, a rail, and an embossment, wherein the one or more features of the inner pouch interact with the handle of the microarray holder, the one or more features of the microarray holder, or both the handle and the one or more features of the microarray holder, to align the microarray holder with respect to the opening in the inner pouch and the opening in the outer pouch.

14. The packaging article of claim 13, wherein the microarray holder is aligned such that the handle is oriented towards the opening in the inner pouch and the opening in the outer pouch.

* * * * *